United States Patent [19]

Thoms et al.

[11] Patent Number: 5,556,883
[45] Date of Patent: Sep. 17, 1996

[54] USE OF HEXAFLUMURON AS A TERMITICIDE

[75] Inventors: Ellen M. Thoms, Tampa, Fla.; Ronald J. Sbragia, Carmel, Ind.

[73] Assignee: DowElanco, Indianapolis, Ind.

[21] Appl. No.: 439,389

[22] Filed: May 11, 1995

Related U.S. Application Data

[63] Continuation of Ser. No. 214,067, Mar. 16, 1994, abandoned, which is a continuation of Ser. No. 891,610, Jun. 1, 1992, abandoned.

[51] Int. Cl.$^6$ .................................................. A01N 47/28
[52] U.S. Cl. ................................................................ 514/594
[58] Field of Search .............................................. 514/594

[56] References Cited

U.S. PATENT DOCUMENTS

| | | | |
|---|---|---|---|
| 4,468,405 | 8/1984 | Rigterink et al. | 424/322 |
| 4,533,676 | 8/1985 | Sirrenberg et al. | 514/535 |
| 4,711,905 | 12/1987 | Sirrenberg et al. | 514/522 |
| 4,833,158 | 5/1989 | Twydell et al. | 514/616 |

FOREIGN PATENT DOCUMENTS

| | | |
|---|---|---|
| 088343A2 | 1/1983 | European Pat. Off. . |
| 2166134A | 4/1986 | United Kingdom . |

OTHER PUBLICATIONS

Von H. Doppelreiter et al., *Entwicklungshemmung durch Diflubenzuron bei den Bodentermiten Heterotermes indicola und Reticulitermes flavipes*, Z. ang. Ent. 91, Verlan Paul Parcy, Hamburg und Berlin, (1981), 131–137.

*Primary Examiner*—Allen J. Robinson
*Attorney, Agent, or Firm*—Alice A. Brewer; Donald R. Stuart

[57] ABSTRACT

Method of using specific acyl urea compounds as termiticides. The compounds are unusually non-repellant to termites and active at low dosages.

10 Claims, No Drawings

USE OF HEXAFLUMURON AS A TERMITICIDE

CROSS-REFERENCE TO RELATED APPLICATION

This is a continuation of application Ser. No. 08/214,067, filed Mar. 16, 1994, now abandoned, which is a continuation of application Ser. No. 07/891,610, filed Jun. 1, 1992, and now abandoned.

BACKGROUND OF THE INVENTION

Termites, insects of the order *Isoptera*, live almost exclusively on cellulose in vegetable matter. However, they can cause considerable damage to other materials in their quest for cellulose, including structural damage to buildings, destruction of foods such as growing crops, grassland, forestry (especially young saplings), household goods, stored food, cellulose based materials such as wood, paper, cotton, fiber matter, and the like. The tendency to attack each of the above materials will vary from species to species.

Damage to structures or other materials may be prevented or diminished by the use of insecticidal compounds active against termites. Such compounds are conventionally applied either to the termite infested material itself or to its component members, e.g., by treatment of timber components before incorporation of the timber into the building, or to soil area surrounding the building.

The majority of commercially available insecticides do not have the combination of biological and physicochemical properties necessary for effective termite control (e.g., activity against termites combined with long-term persistence), although the chlorinated hydrocarbon aldrin has proved effective.

However, increased regulatory controls on chlorinated hydrocarbons have created a need for a termiticide which combines the necessary activity and persistence with a low mammalian toxicity.

Certain acyl urea compounds are claimed to be effective against termites. For instance, U.S. Pat. No. 4,833,158 claims flufenoxuron as a termiticide; and diflubenzuron has also been disclosed specifically as a termiticide.

Hexaflumuron (N-(((3,5-dichloro-4-(1,1,2,2-tetrafluoroethoxy)phenyl)-amino)carbonyl)- 2,6-difluoro benzazmide), a compound with a low mammalian toxicity, has been described as possessing insecticidal activity against insects from the orders *Lepidoptera, Coleoptera, Diptera, Orthoptera, Homoptera, Thysanoptera*, and *Acarina* (U.S. Pat. No. 4,468,405). It has now been found that hexaflumuron and other structurally related compounds are surprisingly more effective as a termiticide than structurally unrelated acyl urea compounds such as, for instance, diflubenzuron.

DESCRIPTION OF THE INVENTION

The present invention provides a method for treating a locus for termites which comprises applying to the locus a compound of the formula

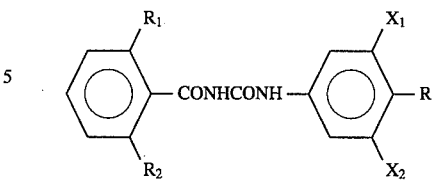

FORMULA I wherein $R_1$ and $R_2$ are each independently hydrogen, $C_1$–$C_3$ alkyl or $C_1$–$C_3$ alkoxy, chloro, bromo or fluoro; $X_1$ and $X_2$ are each independently chloro, fluoro, bromo, hydrogen or $C_1$–$C_3$ alkyl; and R is a fluorine containing $C_1$–$C_4$ haloalkoxy group.

Processes for preparation of the compounds of Formula I are readily available.

The advantage and surprising effect of the use of a compound of Formula I as a termiticide lies in its efficacy at surprisingly low doses and its unique non-repellant effect on termites even at high concentrations. Known methods of termite treatment necessitate the use of relatively large amounts of termiticide to create a physical barrier of relatively high chemical concentrations sufficient to kill some insects and deter others from immediately reinfesting the treated locus by causing those termites to move to an untreated location. The present invention effectively eliminates termite populations by allowing a large number of termites to actually visit, contact and carry away a small but efficacious amount of the non-repellant, termiticidal compound.

In order to facilitate the application of the compounds of Formula I to the desired locus, or to facilitate storage, transport or handling, the compound is normally formulated with a carrier and/or a surface-active agent.

A carrier in the present context is any material with which the compound of Formula I (active ingredient) is formulated to facilitate application to the locus, or storage, transport or handling. A carrier may be a solid or a liquid, including a material which is normally gaseous but which has been compressed to form a liquid. Any of the carriers normally used or known to be usable in formulating insecticidal compositions may be used.

Compositions according to the invention contain 0.0001 to 99.9% by weight active ingredient. Preferably, compositions according to the invention contain 0.001 to 10.0% by weight of active ingredient though proportions as low as 0.0001% may be useful in some circumstances.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example superphosphates. Cellulose based materials, for example wood, sawdust, agar or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable.

Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone. Mixtures of different liquids are often suitable, for example a mixture of isophorone with a polar organic solvent such as N-methylpyrrolidone, as are mixtures of solid and liquid carriers.

Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sufonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfinated castor oil, and sodium alkylaryl sulfonates such as dodecylbenzene sulfonate; and polymers of ethylene oxide and copolymers of ethylene oxide and propylene oxide.

Pesticidal compositions may for example be formulated as wettable powders, dusts, granules, baits, solutions, emulsifiable concentrates, emulsions, suspension concentrates and aerosols.

Wettable powders usually contain 25, 50 or 75% weight of active ingredient and usually contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.5–10% weight of active ingredient.

Granules are usually prepared to have a size between 10 and 100 BS mesh (1.676–0.152 mm), and may be manufactured by, for example, agglomeration or impregnation techniques. Generally, granules will contain 0.01–75% weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent.

Baits are prepared by, for example, combining a mixture of a finely divided cellulose material, such as sawdust, with an amount of active ingredient sufficient to provide the desired result; for example, from about 0.001% to about 20% weight active ingredient and forming the mixture into a paste by the addition of about 1% to 5% of a water based binder such as agar. The paste-like mixture is packed into a housing such as a hollowed out wooden dowel. Baits are a preferable embodiment of the present invention.

Wood or timber is impregnated with active ingredient according to well known procedures including pressure treatments such as the Lowery empty cell process and full cell process, vacuum treatments, hot and cold bath treatment, thermal treatment, and cold-soak treatment. Surface treatment of wood or timber is accomplished by well known techniques such as brushing, dipping, spraying or short-soaking the wood material with active ingredient or appropriate compositions thereof in amounts and in a manner that would be apparent to one skilled in the art.

For instance, wood treatments may be accomplished by two major methods: impregnation of the wood through vacuum and pressure treatments and surface treatments such as painting, spraying or dipping. In an impregnation method, a concentrate may be formulated which contains 1–65% weight per volume active ingredient, 5–50% solvent and, when necessary, co-solvent, and 0–20% w/v of other additives such as penetrants. For treatment, vacuum is pulled on a vessel containing the wood. The concentrate is then added to the vessel and subsequently pressurized to force concentrate into the wood. The vessel is relieved of pressure and the treated wood then removed. In a surface treatment, the concentrate may be simply painted onto a wood surface by means of brushing or spraying or, preferably, dipping. Solvents used for these types of treatments may include polyethylene glycol, and aromatic solvents, and the like due to their ability to penetrate wood.

Emulsifiable concentrates usually contain, in addition to a solvent and, when necessary, co-solvent, 10–50% weight per volume active ingredient, 2–20% weight per volume emulsifiers and 0–20% weight per volume of other additives such as stabilizers, penetrants and corrosion inhibitors.

Suspension concentrates are usually compounded so as to obtain a stable, non-sedimenting flowable product and usually contain 10–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency.

Termiticidal compositions may also contain other ingredients, for example further active compounds possessing herbicidal, insecticidal or fungicidal properties, in accordance with the requirement of the locus to be treated and the treatment method.

The method of applying a compound of Formula I to combat termites comprises applying the compound, conveniently in a composition comprising the compound of Formula I and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combatting termite infestation. This dosage is dependent upon many factors, including the carrier employed, the method and conditions of the application, whether the formulation is present at the locus in the form of a film, or as discrete particles or as a bait, the thickness of film or size of particles, the degree of termite infestation, and the like.

Proper consideration and resolution of these factors to provide the necessary dosage of the active ingredient at the locus to be protected are within the skill of those versed in the art. In general, however, the effective dosage of the compound of the invention at the locus to be protected—i.e., the dosage to which the termite has access—is of the order of 0.001 to 1.0% based on the total weight of the composition, though under some circumstances the effective concentration may be as little as 0.0001% or as much as 2%, on the same basis.

In one embodiment of this invention, the compounds of Formula I are used to combat termites in the soil, thereby achieving indirect protection for any timber-based constructions erected on the treated soil or to crops, grassland, forestry (especially young saplings), and other cellulose based materials surrounded by or located in the treated soil. Suitable soil-based control of termites is obtained by providing in the soil a termiticidaly effective dosage of a compound of Formula I. For use in this manner, the active ingredient is suitably applied to the soil at a rate of from about 0.01 gram to about 10 kilograms per hectare. Depending on the composition used, good control of soil inhabiting termites is obtained at rates of from about 0.01 gram to about 1 kilogram per hectare and preferably from about 0.1 gram to 100 grams per hectare. The compound of Formula I can conveniently be formulated for use as a compound-impregnated wooden stake, bait, granule or powder containing a solid diluent, or as a suspension concentrate. Such formulation usually contain from about 0.001 to about 50% by weight of the compound. Effective control results when the formulation is physically integrated into the topsoil as well as when it is applied to the surface of the soil.

The compound of formula I can also be applied as a drench—that is, as a solution or dispersion of the compound in a suitable solvent or liquid diluent. Such drenches can be prepared by diluting with water a concentrate containing the compound of Formula I, an emulsifying agent, and preferably an organic solvent, such as isophorone and/or N-methylpyrrolidone. The compound of formula I can be applied by band, furrow or side-dress techniques, and may be incorporated or not.

In another embodiment of the invention, compounds of Formula I are applied directly on or into the material to be protected or treated. For example, timber is treated either before, during or after its incorporation into a structure or building, thereby protecting it against damage from termite attack or combating an already existing infestation of termites. For treatment of timber, the composition may contain a penetrant designed to facilitate penetration of the active ingredient to a significant depth in the timber, thereby ensuing that superficial-surface abrasion will not generate a surface free from active ingredient and thus vulnerable to termite penetration.

Examples of materials known for use as wood penetrants include paraffinic hydrocarbons, for instance low aromatic white spirit, 2-ethoxyethanol and methyl isobutyl ketone. Preferably the penetrant is 2-ethoxyethanol or methyl isobutyl ketone, optionally in association with isophorone and/or N-methyl pyrrolidone. It is useful in such timber treatment to incorporate "anti-bloom" agent, which counteract the tendency for the active ingredient to migrate to the surface ("blooming"), suitable materials being dibutyl phthalate and o-dichlorobenzene.

Timber treatment compositions may also, if desired, contain fungicides (to prevent fungal attacks such as dry rot and wet rot), and/or pigments in order to combine termite protection with painting of the timber. In this context, painting will be understood to include not only the application of covering pigmentation (commonly white), but also the application of natural wood coloration in order to restore the appearance of weathered timber (e.g., as with treatments to red cedar external housing timbers).

The actual application onto or into the timber may be carried out using conventional techniques including immersion of the timber in the liquid, painting the liquid onto the timber by spray or brushing, and injecting the liquid into the timber.

The concentration of active ingredient in the treated timber should, of course, be sufficient to achieve desired termiticidal effect. However, the total volume of formulated product taken up by the timber is limited by the absorption properties of the wood with respect to that formulation and will also vary according to the application procedure adopted (immersing, painting or injecting); hence the concentration of active ingredient in the formulation should be such as to produce the desired concentration in the treated timber. The formulation may be aqueous, as for example obtained by dilution of a conventional insecticide emulsifiable concentrate, or non-aqueous such as an undiluted emulsifiable concentrate. The organic solvent in such formulations will suitably be one of those previously described.

The determination of the necessary parameters applicable to specific types of wood and particular treatment procedures can readily be determined by established techniques conventionally used by those skilled in the art. In general, however, the effective dosage of the compound in the wood may be as low as 0.1 ppm, with the maximum dosage dictated by cost considerations rather than biological efficacy.

The invention is illustrated in the following examples:

EXAMPLE 1

Comparative Efficacy of Hexaflumuron and Diflubenzuron

A unit comprised a screw-top glass jar (6.0 cm diam. by 6.5 cm high) in which two 8 $cm^3$ wood (*Pinus* spp.) cubes were placed 1.5 cm apart, covered with 75 $cm^3$ of acetone-washed sand and moistened with 18 ml of deionized water. One wood cube was previously treated with an acetone solution of hexaflumuron or diflubenzuron at concentrations ranging from 1 to 1000 ppm (wt/vol).

One hundred workers (undifferentiated larvae of at least third instar) plus five soldiers of *C. formosanus* were placed in each experimental unit. Termites were previously collected from three field colonies. Units were held at 28°±1° C. After 6 and 9 weeks, three units per treatment were disassembled, the surviving termites counted and ecdysis inhibitory effects on termites were recorded. Treatments were replicated three times per sample interval with each replicate representing a different termite colony. The results are summarized in Table I.

TABLE I

Percent Mortality of *C. formosanus*
(± standard error)

| Concentration (ppm) | 6 weeks | | 9 weeks | |
|---|---|---|---|---|
| | #1 | #2 | #1 | #2 |
| 0 | 15.0 ± 2.4 | 17.3 ± 8.3 | 16.3 ± 1.9 | 26.0 ± 11.5 |
| 7.8 | 66.5 ± 12.5 | 22.7 ± 4.7 | 80.3 ± 9.3 | 34.3 ± 4.3 |
| 15.6 | 65.0 ± 4.2 | 15.0 ± 7.8 | 87.8 ± 8.4 | 27.7 ± 14.2 |
| 31.3 | 68.3 ± 7.4 | 18.3 ± 5.8 | 92.3 ± 7.5 | 44.7 ± 27.7 |
| 62.5 | 78.0 ± 6.1 | 17.3 ± 6.9 | 100.0 ± 0 | 22.0 ± 4.5 |
| 125.0 | 86.7 ± 3.9 | 18.0 ± 5.0 | 100.0 ± 0 | 26.0 ± 4.7 |
| 250.0 | 84.8 ± 4.1 | 18.7 ± 5.2 | 99.7 ± 0.3 | 45.0 ± 16.1 |
| 500.0 | 80.7 ± 3.5 | 23.3 ± 4.7 | 99.7 ± 0.3 | 50.7 ± 24.7 |
| 1000.0 | 92.0 ± 3.1 | 35.0 ± 17.0 | 100.0 ± 0 | 52.3 ± 23.2 |

1 is Hexaflumuron and #2 is Diflubenzuron

This data demonstrates the surprisingly and significantly greater efficacy of hexaflumuron versus diflubenzuron. After 6 weeks, mortality ranged from 65-92% following exposure to hexaflumuron, compared to 15-35% mortality following exposure to diflubenzuron. Only hexaflumuron induced high mortality of 99-100% compared to the highest mortality of 52% after 9 weeks exposure to 1000 ppm diflubenzuron.

EXAMPLE 2

Efficacy of Bait Containing Hexaflumuron against
*C. formosanus* and *R. flavipes*

Cellulose powder (pulverized sawdust of southern yellow pine, *Pinus* sp.) was impregnated with acetone solution of hexaflumuron at concentrations of 0; 31.3; 62.5; 125; 500; 1000; 2000; 4000; and 8000 ppm (wt active ingredient/dry wt bait) for *R. flavipes* and 0; 125; 250; 500; 1000; 2000; 4000; 8000 and 16,000 ppm for *C. formosanus*. Water and agar solution were added to the dry cellulose powder to yield a bait matrix that contained 78% water and 2% agar. The experimental units were comprised of screw-top glass jars (6.0 cm diam. by 6.5 cm high) in which two plastic containers (1.9 cm diam by 2.4 cm high) were placed about 1 cm apart and covered with 75 ml acetone washed sand and 18 ml deionized water. Eight holes (0.238 cm ID) were pre-drilled on the side of the plastic container about 0.5 cm from the bottom to allow termite entry. One container contained treated bait, the other contained untreated bait matrix. The wet weight of bait placed in each plastic container was determined before use. Twenty seven units were prepared for each concentration. One hundred workers (plus 10 soldiers for *C. formosanus* and one soldier for *R. flavipes*) were placed in each unit and held at 28°±1° C. For each termite species, the test was replicated nine times using termites collected from three colonies at three different dates. Nine units per treatment were disassembled at 3, 6, and 9 weeks. The number of surviving termites and those with molting inhibitory effects were counted. The remaining bait was extracted from the plastic container and reweighed. Differences in bait consumption between treated and untreated bait were compared by a paired t test. These results demonstrate that even at the lowest concentrations (31.3 ppm and 62.5 ppm for *R. flavipes* and 125 ppm for *C. formosanus*) termites acquired a sufficient dose of hexaflumuron to exhibit molting inhibition at 6 weeks and mortality at 9 weeks. These results suggest that the threshold concentration for molting inhibition and lethality is low (probably <10 ppm for *R. flavipes* and <100 ppm for *C. formosanus*)

The concentration threshold for feeding deterrence is high: >4000 ppm and >8000 ppm for *R. flavipes* and *C. formosanus*, respectively.

EXAMPLE 3

Hexaflumuron Bait Composition

| Hexaflumuron | 0.1% w/v |
|---|---|
| Sawdust | 30.0% |
| Methocel ® | 1.0% |
| Water | 68.9% |

EXAMPLE 4

Efficacy of Field Bait Containing Hexaflumuron

Pine or spruce sawdust was impregnated with an acetone solution of hexaflumuron to yield concentrations of 500–5,000 ppm (dry wt AI/dry wt sawdust) upon evaporation of acetone. The bait matrix was composed of 20% treated sawdust and 80% of agar or Methocel® solution (2%). A bait station was composed of a plastic tubing (2.9 cm diam. I.D. by 16.5 cm high, one end closed, the other end open) filled with approximately 80 g of bait matrix. Six rows of holes (0.238 mm diam) were pre-drilled on the side of the tubing.

Baits were placed into the ground where termites of the species *R. flavipes* or *C. formosanus* were known to be foraging, and were checked monthly for amount bait matrix consumed.

A. Termite infestation of door and door frame in Plantation, Fla.: Three baits were introduced in February 1991. By April 1991, no termite activity was found in the vicinity. A total of 26 g of bait matrix was consumed: amount of active ingredient consumed was 3.87 mg. Due to absence of termite activity since that time, it is concluded that the entire colony of over 400,000 termites was eliminated by the consumption of 3.87 mg of hexaflumuron within two months.

B. Termite infestation in trees and fallen logs, Plantation, Fla.: Eleven baits were introduced in April 1991. In June 1991, no termites were detected in the area. During the three months (April–June), 122 g bait matrix/20 mg AI was consumed to eliminate a colony of approximately 730,000 *R. flavipes* termites.

C. Structural termite infestation in Plantation, Fla.: Structural infestation of *R. flavipes* colony persisted in a two-story apartment building (approx 1,500 m$^2$) since 1987. Residents reported annual spring swarming from the structure for five consecutive years despite annual traditional termiticide treatments since 1986. Following the introduction of 27 baits in August 1991, the termite activity was reduced to 0.1 g/bait/day in September 1991. More baits were placed. By November 1991, no termite activity was detected. During the four-month period (August–December), a total of 69 baits were used from which 2,997 g bait matrix/i,539 mg AI was consumed by the *R. flavipes* colony to eliminate over 2.5 million termites.

D. Structural termite infestation in Plantation, Fla.: Despite repeated soil termiticide treatments and a fumigation following the discovery of structural infestations by *C. formosanus* in a high rise in 1987, foraging activity remained strong throughout 1989 and 1991. Activity of this colony did not decline even in winter months. Eight baits were introduced in May 1991, and over 90% of the bait matrix were consumed within a month. Foraging activity from May–July was slightly reduced. However, since November 1991, no termite activity has been recorded. During the 6 month baiting period (May–November), 89 baits were used from which 3.405 g of bait matrix/742 mg AI was consumed, which eliminated a colony of about 2.4 million *C. formosanus* termites.

EXAMPLE 5

Solution for Pressure Treatment of Timber

| Active ingredient | 5–50% |
|---|---|
| Solvent | 10–50% |
| Co-solvent | 10–50% |
| Penetrant | 2–10% |
| Surface active agent | 2–10% |

Pressure treatment of timber is accomplished by placing wood to be treated into an appropriate vessel, pulling a vacuum on the vessel, adding the above described solution or a dilution thereof in oil or water, pressurizing the vessel for an appropriate period of time and removing the wood from the vessel after the pressure has been relieved.

In like manner, a solution such as that described above may be used for dipping wood to be treated in the solution, painting or spaying the solution on the wood and allowing the wood to dry.

It should be apparent to one skilled in the art that various modifications may be made in the present invention as described herein without departing from the spirit or the scope of the invention.

What is claimed is:

1. A method for treating a locus for termites which comprises applying to an infested locus an effective amount of a compound of the formula

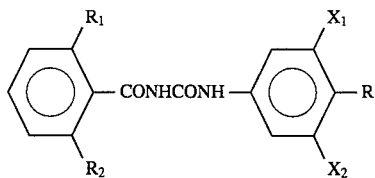

wherein $R_1$ and $R_2$ are each independently hydrogen, $C_1$–$C_3$ alkyl, $C_1$–$C_3$ alkoxy, chloro, bromo or fluoro; $X_1$ and $X_2$ are each independently chloro, fluoro, bromo, hydrogen or $C_1$–$C_3$ alkyl; and R is a fluorine containing $C_1$–$C_4$ haloalkoxy group.

2. A method of claim 1 wherein said locus comprises soil or timber.

3. A method of claim 2 wherein $R_1$ is fluoro or chloro; $R_2$ is hydrogen, fluoro or chloro and R is $OCF_3$, $OCF_2CHF_2$; $OCF_2CHClF$, $OCF_2CFHBr$; $OCF_2CHFCl$; $OCFClCHFCl$; OR $OCF_2CHCl_2$.

4. A method of claim 3 wherein $X_1$ and $X_2$ are Cl; $R_1$ is F or Cl; $R_2$ is F or H and R is $OCF_2CHF_2$, $OCF_2CHFCl$ or $OCF_2CHFBr$.

5. A method of claim 4 wherein $R_1$ and $R_2$ are both F and R is $OCF_2CHF_2$.

6. A method of claim 2 wherein said soil or timber is treated with a composition comprising the compound and a carrier.

7. A method of claim 6 wherein $R_1$ is fluoro or chloro; $R_2$ is hydrogen, fluoro or chloro and R is $OCF_3$, $OCF_2CHF_2$; $OCF_2CHClF$, $OCF_2CFHBr$; $OCF_2CHFCl$; $OCFClCHFCl$; OR $OCF_2CHCl_2$.

8. A method of claim 7 wherein $X_1$ and $X_2$ are Cl; $R_1$ is F or Cl; $R_2$ is F or H and R is $OCF_2CHF_2$, $OCF_2CHFCl$ or $OCF_2CHFBr$.

9. A method of claim 8 wherein $R_1$ and $R_2$ are both F and R is $OCF_2CHF_2$.

10. A method of claim 6 wherein said carrier comprises wood.

\* \* \* \* \*

(12) REEXAMINATION CERTIFICATE (4656th)
United States Patent
Thoms et al.

(10) Number: US 5,556,883 C1
(45) Certificate Issued: Oct. 15, 2002

(54) USE OF HEXAFLUMURON AS A TERMITICIDE

(75) Inventors: Ellen M. Thoms, Tampa, FL (US); Ronald J. Sbragia, Carmel, IN (US)

(73) Assignee: Dowelanco, Indianapolis, IN (US)

Reexamination Request:
No. 90/005,717, May 2, 2000

Reexamination Certificate for:
Patent No.: 5,556,883
Issued: Sep. 17, 1996
Appl. No.: 08/439,389
Filed: May 11, 1995

(21) Appl. No.: 08/439,389

Related U.S. Application Data

(63) Continuation of application No. 08/214,067, filed on Mar. 16, 1994, now abandoned, which is a continuation of application No. 07/891,610, filed on Jun. 1, 1992, now abandoned.

(51) Int. Cl.[7] .................................. A01N 47/34
(52) U.S. Cl. .................. 514/594; 424/405; 424/406; 424/408; 424/409; 424/413; 424/DIG. 11; 424/84
(58) Field of Search ................. 424/405–413, 424/84, DIG. 11; 514/594

(56) References Cited

U.S. PATENT DOCUMENTS 4,533,676 A  8/1985  Sirrenberg et al.
4,833,158 A  5/1989  Twydell et al.

FOREIGN PATENT DOCUMENTS

GB  2 232 798      5/1990
WO  WO 98/34481   8/1998

OTHER PUBLICATIONS

Ahmad, et al., "Prelimimary Studies on the Effects of Diflubenzuron (Dimilin) on Termites (Isoptera)." *Pakistan J. Zool.* 18:403–09 (1986).

Doppelreiter, H. and Korioth, M., "Inhibition of Development of the Subterranean Termites *Heterotemes indicola* and *Reticulitermes flavipes* Caused by Diflubenzuron (Dimilin[R])." *Plant Research and Development* 15: 103–10 (1982).

Su, N.–Y– and Scheffrahn, R.H., "Laboratory evaluation of two chitin synthesis inhibitors, hexaflumuron and diflubenzuron, as bait toxicants against formosan and eastern subterranean termites (Isoptera: Rhinotermitidae)." *J. Econ. Entomol.* 86(5): 1453–57 (1993).

Su, N.–Y., "Field Evaluation of a Hexaflumuron Bait for Population Suppression of Subterranean Termites (Isoptera: Rhinotermitidae)." *J. Econ Entomol.* 87(2): 389–97 (1994).

Su, N.–Y. and Scheffrahn, R.H., "Comparative effects of two chitin synthesis inhibitors, hexaflumuron and lufenuron, in a bait matrix against subterranean termites (Isoptera: Rhinotermitidae)." *J. of Econ. Entomol.* 89(5): 1156–60 (1996).

*Primary Examiner*—Neil S. Levy

(57) ABSTRACT

Method of using specific acyl urea compounds as termiticides. The compounds are unusually non-repellant to termites and active at low dosages.

REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–9 are cancelled.

Claim 10 is determined to be patentable as amended.

New claims 11–24 are added and determined to be patentable.

10. A method [of claim 6] *for treating a locus for termites* which comprises applying to an infested locus an effective amount of a compound of the formula $$\text{F-C}_6\text{H}_3\text{F-CONHCONH-C}_6\text{H}_2\text{Cl}_2\text{-OCF}_2\text{CHF}_2$$

wherein *said locus comprises soil or timber and wherein said soil or timber is treated with a composition comprising the compound and a carrier and* wherein said carrier comprises wood.

*11. A method for treating a locus for termites which comprises applying to an infested locus an effective amount of a compound of the formula*

$$\text{F-C}_6\text{H}_3\text{F-CONHCONH-C}_6\text{H}_2\text{Cl}_2\text{-OCF}_2\text{CHF}_2$$

*wherein said applying is accomplished using a termite bait and wherein said termite bait comprises said effective amount of said compound and wherein said termite bait further comprises wood.*

*12. A method according to claim 11 wherein said locus comprises soil and said termite bait is placed in said soil.*

*13. A method comprising applying a composition to a locus to be treated for termites, wherein:*

*(1) said composition comprises a compound of the following formula*

$$\text{F-C}_6\text{H}_3\text{F-CONHCONH-C}_6\text{H}_2\text{Cl}_2\text{-OCF}_2\text{CHF}_2;$$

*(2) said locus is subject to infestation by termites; and*

*(3) said composition is applied in an amount effective to reduce said termite infestation of said locus.*

*14. A method according to claim 13 wherein said amount produces significantly greater efficacy when compared to diflubenzuron.*

*15. A method according to claim 14 wherein said composition further comprises cellulose.*

*16. A method according to claim 14 wherein said composition further comprises wood.*

*17. A method comprising applying a composition to a locus to be treated for termites, wherein:*

*(1) said composition comprises a compound of the following formula*

$$\text{F-C}_6\text{H}_3\text{F-CONHCONH-C}_6\text{H}_2\text{Cl}_2\text{-OCF}_2\text{CHF}_2;$$

*(2) said locus is subject to attack by termites; and*

*(3) said composition is applied in an amount effective to reduce said termite attacks in said locus.*

*18. A method according to claim 17 wherein said amount produces significantly greater efficacy when compared to diflubenzuron.*

*19. A method according to claim 18 wherein said composition further comprises cellulose.*

*20. A method according to claim 18 wherein said composition further comprises wood.*

*21. A method comprising applying a composition to a locus to be treated for termites, wherein:*

*(1) said composition comprises a non-repellant, termiticidal compound of the following formula*

$$\text{F-C}_6\text{H}_3\text{F-CONHCONH-C}_6\text{H}_2\text{Cl}_2\text{-OCF}_2\text{CHF}_2;$$

*(2) said locus is subject to attack by termites; and*

*(3) said composition is applied in an amount that effectively eliminates termite populations by allowing said termites to visit, contact, and carry away a small efficacious amount of said compound.*

*22. A method according to claim 21 wherein said amount produces significantly greater efficacy when compared to diflubenzuron.*

*23. A method according to claim 22 wherein said composition further comprises cellulose.*

*24. A method according to claim 23 wherein said composition further comprises wood.*

* * * * *